US006962687B1

(12) United States Patent
Pettersson et al.

(10) Patent No.: US 6,962,687 B1
(45) Date of Patent: Nov. 8, 2005

(54) METHOD AND MEANS FOR DETECTING INFLAMMATORY PROCESSES

(75) Inventors: Anders Pettersson, Kode (SE); Thomas Lundqvist, Uppsala (SE)

(73) Assignee: Orexo AB, Uppsala (SE)

( * ) Notice: Subject to any disclaimer, the term of this patent is extended or adjusted under 35 U.S.C. 154(b) by 129 days.

(21) Appl. No.: 10/110,040

(22) PCT Filed: Oct. 24, 2000

(86) PCT No.: PCT/SE00/02054

§ 371 (c)(1),
(2), (4) Date: Aug. 26, 2002

(87) PCT Pub. No.: WO01/31334

PCT Pub. Date: May 3, 2001

(30) Foreign Application Priority Data

Oct. 26, 1999 (SE) .................................. 9903885

(51) Int. Cl.[7] ...................... A61K 51/00; A61M 36/14

(52) U.S. Cl. .................. 424/1.81; 424/1.11; 424/1.37; 424/1.65; 424/9.1

(58) Field of Search ................ 424/1.4, 1.37, 424/1.65, 1.69, 1.81, 9.1, 9.2, 9.3, 9.4, 9.5, 424/9.6, 9.7, 9.8

(56) References Cited

U.S. PATENT DOCUMENTS 6,379,649 B1 * 4/2002 Katsifis et al. ............. 424/1.85

FOREIGN PATENT DOCUMENTS

| DE | 19719098 | 5/1999 |
| WO | WO 96/17244 | 6/1996 |
| WO | WO 97/37587 | 10/1997 |

OTHER PUBLICATIONS

Forte et al, Hypertension (1998), 32(4) 730-734.*
Forte et al., "Measurement of Nitric Oxide Synthesis in Humans Using L-[15N2]Arginine", Methods in Enzymology, vol. 301, pp. 92-98 (1999).

* cited by examiner

*Primary Examiner*—Dameron L. Jones
(74) *Attorney, Agent, or Firm*—Dickstein, Shapiro, Morin & Oshinsky, LLP.

(57) ABSTRACT

A method of detecting inflammatory processes comprises (a) administering per-orally or per-rectally a composition comprising a diagnostically effective amount of L-[guanido-$^{15}N_2$]-arginine, L-[guanido-$^{15}N$]-arginine, their mixtures and pharmaceutically acceptable salts thereof, and a pharmaceutically acceptable carrier; (b) collecting a sample of exhaled air, saliva or urine; (c) determining $^{15}NO$ in the air sample or its transformation products $^{15}N$-nitrite and/or $^{15}N$-nitrate in the saliva sample or urine. Also disclosed is a corresponding diagnostic composition for use in diagnosing inflammatory processes and a method for its manufacture.

10 Claims, No Drawings

METHOD AND MEANS FOR DETECTING INFLAMMATORY PROCESSES

This is a 371 of PCT/SE00/02054, filed Oct. 24, 2000.

FIELD OF THE INVENTION

The present invention relates to a method for determining nitrogen oxide formed in inflammatory processes, to a means for carrying out the method and to a method of manufacture of the means.

BACKGROUND OF THE INVENTION

Nitrogen oxide (NO) has important biological functions. It is the structurally simplest mediator in the human body as well as one of the most important weapons of its immune defense. In its later function it is excreted by activated macrophages to kill foreign microorganisms and cells recognized as foreign. In this second capability nitrogen oxide may be considered an inflammation marker and has been recognized as such in, for instance, inflammatory processes in the gastro-intestinal tract, such as ulcerative colitis and Crohn's disease and celiac disease. In the lung it may assume both roles. It is recognized that levels of nitrogen oxide excretion are raised in asthmatics. Thus it may be considered a marker for asthma which also comprises an important inflammatory component.

In the body nitrogen oxide is formed from L-arginine by hydroxylation of one of the guanidino nitrogens in a reaction catalyzed by one of the isoforms of the enzyme nitrogen oxide synthase (NOS). In a complex reaction the thus formed hydroxyimino intermediate is oxidatively split into nitrogen oxide and L-citrulline.

Nitrogen oxide may be sampled in situ and measured by, for instance, chemoluminescense (WO 96/17244; WO 97/37587). In situ sampling, for instance in the gastrointestinal tract and in the urinary tract, often is difficult or at least time-consuming. Samples of exhaled air may contain nitrogen oxide formed in the pulmonary system but also formed elsewhere because of the considerable solubility of NO in water and lipids which makes it freely diffusible in the body. Increased levels of NO in exhaled air thus may be due to inflammation in the pulmonary system as well as elsewhere. This detracts from the potential usefulness of nitrogen oxide as an inflammation marker.

OBJECTS OF THE INVENTION

It is an object of the invention to provide an improved method for determining nitrogen oxide formed in the body.

It is another object of the invention to provide a means for carrying out said method.

Further objects of the invention will be apparent from the following description of the invention and preferred embodiments thereof, and from the appended claims.

SUMMARY OF THE INVENTION

According to the present invention is provided a method of the aforementioned kind comprising the per-oral or per-rectal administration of a composition comprising a diagnostically effective amount of arginine terminally labeled with the stable nitrogen isotope $^{15}$N for determination, directly or indirectly, of $^{15}$NO in exhaled air or saliva. It is more preferred for both terminal nitrogen atoms to be labeled. In this specification is understood by 'terminally labeled' the labeling of one or both of the terminal guanido nitrogen atoms of L-arginine. Direct determination of $^{15}$NO implies that the compound is measured as such, whereas indirect determination implies that a product into which it has been transformed is measured such as, for instance, $^{15}$N-nitrite or $^{15}$N-nitrate.

According to a first preferred aspect of the invention is provided a method for per-oral administration of a diagnostic composition comprising a diagnostically effective amount of L-arginine terminally labeled with the stable nitrogen isotope $^{15}$N for release in the small intestine and/or in the upper part of the large intestine.

According to a second preferred aspect of the invention is provided a method of the aforementioned kind comprising the per-rectal administration of a composition comprising a diagnostically effective amount of arginine terminally labeled with the stable nitrogen isotope $^{15}$N for release in the lower part of the large intestine.

According to a third preferred aspect of the invention is provided a method of the aforementioned kind comprising the per-oral administration of a diagnostic composition comprising a diagnostically effective amount of L-arginine terminally labeled with the stable nitrogen isotope $^{15}$N for inhalation.

Preferred assaying methods for $^{15}$N comprise: IR-spectrometry, laser spectrometry, gas chromatography and mass spectrometry, and their combinations. The determination of $^{15}$N as NO by any of these methods must take into account the fact that atmospheric nitrogen is a mixture of $^{14}$N (99.63%; isotopic abundance) and $^{15}$N (0.37%). In a sample of exhaled air is thus the amount of $^{15}$N in excess of the natural isotopic abundance of $^{15}$N that is representative of labeled nitrogen in arginine. The determination of $^{15}$N as NO by any of these methods must also take into account the purity of the label. The fact that $^{14}$N and $^{15}$N differ in their mass by 6.6%, in consideration of the natural abundance of $^{16}$O oxygen being 99.76%, makes $^{15}$N particularly attractive as a marker. It is thus $^{15}$N$^{16}$O which is determined at m/e=31 in the presence of $^{14}$N$_2$ (m/e=28), $^{14}$N$^{15}$N (m/e=29), $^{14}$N$^{16}$O (m/e=30) formed from non-labeled L-arginine, $^{16}$O$_2$ (m/e=32), $^{14}$N$^{18}$O (m/e=32), $^{16}$O$^{17}$O (m/e=33), $^{16}$O$^{18}$O (m/e=34). Because of the low natural abundance of $^{17}$O (0.037%) $^{14}$N$^{17}$O (m/e=31) will be present in minute amounts only, and can be disregarded from.

It is advantageous to partially or fully separate the components of a gaseous sample containing $^{15}$NO in a gas chromatograph before injecting a sample of the fraction containing nitrogen oxide in the mass spectrometer. Methods for such separation are well known in the art.

Since NO formed from $^{15}$N$_2$-arginine is isotopically quantitatively different from NO formed from unlabeled arginine, the amount of NO formed at or near the site where the labeled arginine is administered can be determined.

Thus, according to a further preferred aspect of the invention, the site of administration of terminally $^{15}$N-labeled arginine is different from the site of detection of $^{15}$N-labeled NO formed therefrom. For instance, terminally labeled $^{15}$N-arginine can be administered orally or rectally to a person suspected to suffer from ulcerative colitis or Crohn's disease, and the intestinally formed $^{15}$N-labeled NO be determined in the exhaled air or, in the form of nitrite or nitrate, in saliva.

According to still another preferred aspect of the invention labeled nitrogen oxide formed from correspondingly terminally labeled $^{15}$N-arginine can be assayed by measurement of one or several of the products to which it is biologically transformed, in particular nitrate. It is known that a substantial amount of nitrogen oxide entering the bloodstream is oxidized to nitrate in which form it is excreted by the kidneys. It is thus within the scope of the invention to determine the formation of labeled nitrogen oxide by measuring labeled $^{15}NO_3^-$ in urine. Another important path for excretion is from the salivary glands. It is thus also within the scope of the invention to determine the formation of labeled nitrogen oxide from correspondingly $^{15}N$-labeled L-arginine by measuring $^{15}N$-labeled $NO_3^-$ in saliva and/or by measuring $^{15}N$-labeled $NO_2^-$ in saliva to which nitrate is rapidly transformed by the action of certain bacteria colonizing the surface of the tongue.

According to still another preferred aspect of the invention $^{15}N$-labeled arginine can be administered to the lungs in form of a spray or mist for the detection of inflammatory processes in the respiratory system, in particular of asthma, nasal inflammation, and sinusitis.

According to still another preferred aspect of the invention $^{15}N$-labeled arginine can be administered to the circulating blood in form of an injection or infusion for the detection of inflammatory processes in the blood (sepsis) or in tissues in contact with circulating blood.

According to the present invention is also disclosed a diagnostic composition for use in diagnosing inflammatory processes, comprising a diagnostically effective amount of terminally labeled $^{15}N$-arginine and a pharmaceutically acceptable carrier.

Also disclosed is a process for the manufacture of such composition comprising formulating a diagnostically effective amount of terminally labeled $^{15}N$-arginine and a pharmaceutically acceptable carrier into a pharmaceutical composition for per-oral or per-rectal administration.

It is preferred for the compositions according to the invention for per-oral administration to be selected from the group consisting of: enteric delayed release compositions for per-oral administration releasing $^{15}N$-arginine in the small intestine and/or the upper part of the large intestine; nebulizable aqueous solutions of and powders containing terminally labeled $^{15}N$-arginine for administration to the bronchi and the lung.

It is preferred for the compositions according to the invention for per-rectal administration to be selected from enemas, foams, and suppositories.

DESCRIPTION OF PREFERRED EMBODIMENTS

EXAMPLE 1

Terminally N-labeled Arginine

L-[guanido-$^{15}N_2$]-arginine is commercially available from ICN Pharmaceuticals, Inc. (Costa Mesa, Calif.) and Tracer Technology, Inc. (Somerville, Mass.). Fully $^{15}N$-labeled arginine can also be used. It can be produced by *Corynebacterium herculis* or *Brevibacterium flavum* strains carrying the recombinant DNA pCarg11 or pCarg110 according to the method disclosed in U.S. Pat. No. 5,017,482, which is hereby incorporated by reference, with the proviso that $^{15}N_3$ ammonium sulphate is substituted for ammonium sulphate as the nitrogen source. L-[guanido-$^{15}N_2$]-arginine can be used in form of the free base or a pharmaceutically acceptable salt, such as the hydrochloride or aspartate.

EXAMPLE 2

Enteric Tablet

An enteric tablet for release in the small intestine and the upper large intestine can be prepared according to EP 0 502 092 A1 by substituting a terminally N-labeled arginine for any of the glucocorticoids disclosed therein. A suitable amount of terminally N-labeled arginine, such as L-[guanido-$^{15}N_2$]-arginine, is 50 mg, in the form of the free base or a pharmaceutically acceptable salt thereof, such as the hydrochloride.

EXAMPLE 3

Suppository

A suitable type of suppository can be made by use of the Salazopyrin® EN, Pharmacia & Upjohn, enema composition in which the active principle sulfasalazine (500 mg) is exchanged for 50 mg L-[guanido-$^{15}N_2$]-arginine and 450 mg of suitable neutral constitutents, such as calcium carbonate.

EXAMPLE 4

Solution for Inhalation Spray 100 mg L-[guanido-$^{15}N_2$]-arginine are dissolved in 10 ml of sterile water. The solution is administered by a nebulizer capable of dispensing measured doses.

EXAMPLE 5

Determination of Inflammatory Conditions in the Small Intestine and the Upper Part of the Large Intestine An enteric tablet of EXAMPLE 2 is administered to the person suspected of inflammation in a fasting state. Breath samples (100 ccm) are taken in 10 min intervals starting at time of administration.

EXAMPLE 6

Determination of Inflammatory Conditions in the Lower Part of the Large Intestine A suppository of EXAMPLE 3 is per-rectally administered to the person suspected of inflammation being in a fasting state. Breath samples (100 ccm) are taken in 10 min intervals starting at time of administration.

EXAMPLE 7

Determination of Inflammatory Conditions in the Lung

A metered dose (1 ccm) of the solution for inhalation of EXAMPLE 4 is nebulized for inhalation by the patient using of a state-of-the-art nebulizer. Breath samples (100 ccm) are taken in 5 min intervals starting at time of administration.

EXAMPLE 7

Determination of Inflammatory Conditions in the Blood

An intravenous infusion of L-[guanido-$^{15}N_2$]-arginine is administered to a person suspected of sepsis. Breath samples (100 ccm) are taken in 10 min intervals starting at time of administration.

EXAMPLE 8

Determination of $^{15}$NO in Gaseous Samples

See: D C Macallan et al., Am. J. Physiol. 272 (6, part 2), p. R1888–R1896 (1997).

EXAMPLE 9

Determination of Urinary $^{15}$NO$_3^-$

See: P Forte et al., Measurement of Nitric Oxide Synthesis in Humans Using L-[$^{15}$N$_2$]Arginine. Methods in Enzymology 301 (1999) 92–98. The method is easily modified for measurement of nitrate in saliva.

What is claimed is:

1. A method of detecting the existence of an inflammatory process comprising:
    administering by inhalation to a person a composition comprising a diagnostically effective amount of L-[guanido-$^{15}$N$_2$]-arginine, L-[guanido$^{15}$N]-arginine, their mixtures and pharmaceutically acceptable salts thereof, and a pharmaceutically acceptable carrier,
    collecting a sample of exhaled air, saliva or urine,
    determining $^{15}$NO in the air sample or its transformation products $^{15}$N-nitrite and/or $^{15}$N-nitrate in the saliva sample or urine,
    wherein the inflammatory process is asthma or a bacterial or viral infection of the respiratory system.

2. The method of claim 1, wherein the composition administered is a spray or mist for inhalation from an aqueous solution of L-[guanido-$^{15}$N$_2$]-arginine, L-[guanido-$^{15}$N]-arginine, their mixtures, and pharmaceutically acceptable salts thereof.

3. The method of claim 1, wherein the composition administered is a inhalation suspension in air from a powder comprising L-[guanido-$^{15}$N$_2$]-arginine, L-[guanido-$^{15}$N]-arginine, their mixtures and pharmaceutically acceptable salts thereof.

4. The method of claim 1, wherein said amount is from 1 mg to 2,000 mg.

5. The method of claim 1, wherein the sample collected is exhaled air or saliva.

6. The method of claim 1, wherein determination is by IR-spectrometry, laser spectrometry, mass spectrometry, gas chromatography, and their combinations.

7. The method of claim 6, wherein the sample collected is exhaled air or saliva.

8. The method of claim 7, wherein said amount is from 1 mg to 2,000 mg.

9. The method of claim 8, wherein the composition administered is a spray or mist for inhalation from an aqueous solution of L-[guanido-$^{15}$N$_2$]-arginine, L-[guanido-$^{15}$N]-arginine, their mixtures, and pharmaceutically acceptable salts thereof.

10. The method of claim 8, wherein the composition administered is a inhalation suspension in air from a powder comprising L-[guanido-$^{15}$N$_2$]-arginine, L-[guanido-$^{15}$N]-arginine, their mixtures and pharmaceutically acceptable salts thereof.

* * * * *